United States Patent [19]

Hooper et al.

[11] 4,288,341

[45] Sep. 8, 1981

[54] DETERGENT PRODUCT CONTAINING DEODORANT COMPOSITIONS

[75] Inventors: David C. Hooper, Ashford; George A. Johnson; Donald Peter, both of Wirral, all of England

[73] Assignee: Lever Brothers Company, New York, N.Y.

[21] Appl. No.: 933,943

[22] Filed: Aug. 15, 1978

[30] Foreign Application Priority Data

Mar. 20, 1978 [GB] United Kingdom ............... 10969/78
May 16, 1978 [GB] United Kingdom ............... 19841/78

[51] Int. Cl.$^3$ .......................... C11D 9/44; C11D 9/50
[52] U.S. Cl. .................................... 252/107; 252/106; 252/108; 252/132; 252/174.11
[58] Field of Search .................... 252/89 R, 107, 108, 252/106, 132, 174.11; 424/65

[56] References Cited

U.S. PATENT DOCUMENTS

| | | | |
|---|---|---|---|
| 2,875,131 | 2/1959 | Carpenter et al. | 252/522 X |
| 2,889,254 | 6/1959 | Fiore et al. | 252/522 X |
| 2,918,412 | 12/1959 | Wood | 252/522 X |
| 2,976,321 | 3/1961 | Dorsky et al. | 252/522 X |
| 3,144,467 | 8/1964 | Houlihan | 260/343.2 |
| 3,268,594 | 8/1966 | Bedoukian | 260/615 |
| 3,317,397 | 5/1967 | Saunders | 252/108 X |
| 3,318,945 | 5/1967 | Erman | 260/468 |
| 3,493,650 | 2/1970 | Dunkel | 424/65 |
| 3,591,643 | 7/1971 | Fanta et al. | 260/617 F |
| 3,662,007 | 5/1972 | Fanta et al. | 260/631.5 |
| 3,679,756 | 7/1972 | Kretschmar et al. | 260/631.5 |
| 3,684,723 | 8/1972 | Best et al. | 252/132 |
| 3,836,232 | 10/1974 | Ohloff et al. | 252/522 |
| 3,862,049 | 1/1975 | McGarth et al. | 252/108 |
| 3,969,259 | 7/1976 | Lages | 252/107 |
| 4,055,506 | 10/1977 | Pittet et al. | 252/132 |
| 4,066,710 | 1/1978 | Ochsner | 260/631.5 |
| 4,100,110 | 7/1978 | Ansari et al. | 252/522 |
| 4,129,569 | 12/1978 | Schreiber et al. | 260/307 FA |

FOREIGN PATENT DOCUMENTS

| | | |
|---|---|---|
| 7804601 | 8/1977 | Brazil . |
| 2440025 | 3/1975 | Fed. Rep. of Germany . |
| 2454969 | 5/1975 | Fed. Rep. of Germany . |
| 2461593 | 7/1975 | Fed. Rep. of Germany . |
| 2502767 | 7/1975 | Fed. Rep. of Germany . |
| 2461605 | 10/1975 | Fed. Rep. of Germany . |
| 2516696 | 10/1975 | Fed. Rep. of Germany . |
| 2535576 | 2/1976 | Fed. Rep. of Germany . |
| 2540624 | 4/1976 | Fed. Rep. of Germany . |
| 2455761 | 6/1976 | Fed. Rep. of Germany . |
| 858826 | 1/1961 | United Kingdom . |
| 1085940 | 10/1967 | United Kingdom . |
| 1197817 | 7/1970 | United Kingdom . |
| 1266060 | 3/1972 | United Kingdom . |
| 1282889 | 7/1972 | United Kingdom . |
| 1302933 | 1/1973 | United Kingdom . |
| 1359492 | 7/1974 | United Kingdom . |
| 1420949 | 1/1976 | United Kingdom . |

OTHER PUBLICATIONS

"Handbuch der Kosmetika and Ricchstoffe, Band 2", H. Janistyn, 1969.
"Handbuch der Gesarnten Parfumerie and Kosmetik", Fred Winter, 1952, pp. 735–754.
Sagarin, "Cosmetics—Science & Technology", (M. B. Balsam), Chapter 32, 1972, pp. 599 and 608–621.

*Primary Examiner*—P. E. Willis, Jr.
*Attorney, Agent, or Firm*—James J. Farrell; Melvin H. Kurtz; Irving N. Feit

[57] ABSTRACT

A deodorant toilet bar comprises a soap mixture; optionally, straight chain fatty acids; and a deodorant composition. The bar can be employed for personal washing of the skin and will as a result reduce human body malodor.

16 Claims, No Drawings

DETERGENT PRODUCT CONTAINING DEODORANT COMPOSITIONS

This invention relates to deodorant soap compositions for use in suppressing human body malodour.

BACKGROUND TO THE INVENTION

It has long been recognised that the development of body malodours is at least partly due to bacterial action on the products of the sweat glands. Washing the skin with a personal washing toilet soap bar usually removed some malodorous products and reduces the concentration of bacteria on the skin, but body malodour is likely to redevelop rapidly, particularly if physical activity accompanied by sweating is subsequently undertaken.

It has been customary to incorporate germicides, such as 3,4,4'-trichlorocarbanilide, 3,5,4'-tribromosalicylanilide and 2,4,4'-trichloro-2'-hydroxy diphenyl ether, into personal washing toilet soap bars, in the belief that growth of these skin microflora that contribute to body malodour can be inhibited, and that the subsequent formation on the skin of malodorous substances can be prevented, at least for a few hours. Germicides are thus at least partly effective in reducing or retarding the development of body malodour, but they do not completely solve the problem, possibly because there are other causes of malodour development on the skin which are unrelated to the proliferation of bacteria.

SUMMARY OF THE INVENTION

It has now been discovered that certain combinations of materials other than germicides, hereinafter referred to as "deodorant compositions", when incorporated into the formulation of certain special toilet soap bars intended for personal washing provide a more effective means for inhibiting malodour development on the skin than do germicides.

In the course of attempts to characterise this new principle, many hundreds of materials have been screened. Soap bars containing hundreds of formulations made by blending materials have been examined in order to characterise the new principle.

DEFINITION OF THE INVENTION

In its widest aspect, the invention provides a deodorant toilet soap bar comprising from 0.5 to 99.9% by weight of a soap mixture, from 0 to 15% by weight of $C_6$ to $C_{18}$ straight chain fatty acids and from 0.1 to 10% by weight of a deodorant composition comprising from 45 to 100% by weight of deodorant active components, said components having a lipoxidase-inhibiting capacity of at least 50% or a Raoult Variance Ratio of at least 1.1, said components being classified into six classes consisting of:

Class 1: phenolic substances
Class 2: essential oils, extracts, resins and synthetic oils
Class 3: aldehydes and ketones
Class 4: polycyclic compounds
Class 5: esters
Class 6: alcohols provided that where a component can be classified into more than one class it is placed in the lower or lowest numbered class; said components being selected so that:

(a) the deodorant composition contains at least five components of which at least one must be selected from each of class 1, class 2 and class 4;

(b) the deodorant composition contains components from at least 4 of the 6 classes; and (c) any component present in the deodorant composition at a concentration of less than 0.5% by weight of said composition is eliminated from the requirements of (a) and (b).

The invention also provides a process for preparing a deodorant soap bar which process comprises blending a soap mixture together with if necessary straight chain fatty acids and a deodorant composition as herein defined and thereafter extruding and stamping to provide a deodorant toilet soap bar.

The invention furthermore provides a method for suppressing human body malodour which comprises applying to the human skin in the region of apocrine sweat glands an effective amount of the deodorant composition as herein defined.

It is a preferred property of the deodorant soap bar of the invention that is should comprise a deodorant composition which satisfies a deodorancy test when applied to the skin of human subjects. The average amount by which body malodour should be reduced is expressed in terms of the deodorant value of the deodorant composition contained in the soap bar. Soap bars of the invention accordingly preferably comprise a deodorant composition having a deodorant value of from 0.50 to 3.5. Soap bars in which the deodorant composition has a deodorant value of below 0.50 are outside the scope of this invention and are considered to be incapable of reducing body malodour to a significant extent.

THE DEODORANT VALUE TEST

In this test the deodorant value of a deodorant composition is measured by assessing its effectiveness, when contained in a standard soap bar at a standard concentration, is reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base employed in many of the tests referred to later in this specification is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noddles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and plodded in conventional equipment, cut into billets and stamped into tablets. The deodorant composition to be tested is therefore present at the standard level of 1.5%. These tablets are the test soap bars described as 80/20/5 soap base in the examples, and consist of 80 parts tallow soap and 20 parts coconut soap, 5 parts of this soap mixture being free fatty acids expressed as coconut oil fatty acid.

Examples of alternative soap bars are those prepared in a similar manner except that they consist of 80 parts tallow soap and 20 parts of coconut soap, with no free fatty acid (described as 80/20 soap base), or 55 parts tallow soap and 45 parts of coconut soap, 7.5 parts of this soap mixture being free fatty acids expressed as coconut oil fatty acid (described as 55/45/7.5. soap base).

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include anti-oxidants in the control bar, but these should be present only in the amount required to stabilise the soap base.

The test is conducted as follows:

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the procedure described in Whitehouse and Carter, Proc. Scientific Section of the Toilet Goods Association, 48, 31, (1967).

A panel of 50 human subjects for use in the test is assembled from Caucasian male subjects of age within the range of from 20 to 55 years. By screening, subjects are chosen who develop auxiliary body malodour that is not unusually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour on a scale from 0 to 5, with 0 corresponding to no odour and 5 representing very strong odour. Before evaluation each subject stands with his arms against his side; he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in Table 1 below.

TABLE 1

| Score | Odour Level | Concentrations of aqueous solution of isovaleric acid (ml/1) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

More generally, deodorant values can be determined at other deodorant composition concentrations using a test similar to the test described above, and later in this specification reference is made to deodorant values determined at 1,3 and 5% deodorant composition concentrations.

Although the invention in its widest aspect provides deodorant soap bars comprising deodorant compositions having a deodorant value of from 0.50 to 3.5, preferred deodorant soaps are those comprising deodorant compositions which have a deodorant value of at least 0.60, or 0.70, or 0.80, or 0.90, or 1.00, or 1.10, the higher the minimum value, the more effective is the soap bar as a deodorant soap as recorded by the assessors in the deodorant value test. It has also been noted that consumers, who are not trained assessors, can detect by self-assessment a noticeable reduction in body malodour where the deodorant value is at least 0.90, the higher the deodorant value above this figure, the more noticeable is the deodorant effect.

DEODORANT SOAP BAR MATERIALS

1. The Soap Mixture

Soaps are water soluble salts of higher fatty acids and include alkali metal soaps such as the sodium, potassium, ammonium and alkanol ammonium salts of straight chain saturated or unsaturated fatty acids containing from about 8 to about 24 carbon atoms, and preferably from about 10 to about 20 carbon atoms.

The soap mixture consists of a special mixture of such soaps including the following:

(a) a soap of lauric acid, (b) a soap of myristic acid,
(c) a soap of palmitic acid,
(d) a soap of stearic acid, and
(e) a soap of oleic acid.

Preferably the soap mixture comprises:

(a) from 2 to 35%, most preferably 5 to 25% by weight of a soap of lauric acid, (b) from 0.5 to 25%, most preferably 5 to 10% by weight of a soap of myristic acid, (c) from 5 to 45%, most preferably 20 to 30% by weight of a soap of palmitic acid, (d) from 1 to 25%, most preferably 14 to 18% by weight of a soap of stearic acid, and (e) from 10 to 40%, most preferably 20 to 35% by weight of a soap of oleic acid.

The soap mixture can also comprise soaps of other fatty acids having from 8 to 24 carbon atoms in the molecule, in particular the soaps of dehydrated hardened castor oil fatty acids, and the soaps of erucic and behenic acids.

The preferred soaps are sodium soaps, although a proportion of potassium soaps, ammonium soaps or alkanol ammonium soaps, such as monoethanolamine soaps, can be included in the soap mixture to impart to the finished soap bar a desired degree of softness or plasticity.

The fatty acid soaps can be obtained by the saponification of at least two naturally occurring oils or fats (hereinafter referred to as oils). A proportion of each is present in the soap mixture.

The first oil has the following characteristics:

(a) a saponification value of from 170 to 220, preferably 190 to 210;

(b) an iodine value of from 25 to 70, preferably from 35 to 55;

(c) a fatty acid titre value of from 30° to 55° C., preferably from 40° to 50° C.; and (d) an INS value of from 120 to 210, preferably from 140 to 180.

The first oil, when saponified, also comprises at least 15 parts by weight, preferably 20 to 50 parts by weight of a soap of palmitic acid, at least 2 parts by weight, preferably 3 to 20 parts by weight of a soap of stearic acid and at least 30 parts by weight, preferably 35 to 50 parts by weight of a soap of oleic acid.

The first oil may also comprise a mixture of oils which individually or collectively exhibit the properties and fatty acid analysis as herein defined.

Examples of the first oil are vegetable oils such as Bornea tallow, Chinese vegetable tallow, Illipe butter, mowrah butter and palm oil, and animal oils such as beef tallow, mutton tallow, lard and bovine butter fat.

The first oil, when saponified, forms from 30 to 95% by weight, preferably from 60 to 90% by weight of the soap mixture.

The second oil has the following characteristics:

(a) a saponification value of from 240 to 265, preferably from 245 to 260;

(b) an iodine value of from 5 to 20, preferably from 10 to 15;

(c) a fatty acid titre value of from 15° to 30° C., preferably from 20° to 25° C.; and (d) an INS value of from 220 to 255, preferably from 230 to 250.

The second oil, when saponified, also comprises at least 40 parts by weight, preferably from 45 to 50 parts by weight of a soap of lauric acid and at least 10 parts by weight, preferably from 12 to 25 parts by weight of a soap of myristic acid.

The second oil may also comprise a mixture of oils which individually or collectively exhibit the properties and fatty acid analysis as herein defined.

Examples of the second oil are vegetable oils including coconut oil, palm kernel oil, cohune nut oil, murumuru palm kernel oil, khakan oil and babassu oil.

The second oil, when saponified, forms from 5 to 70% by weight, preferably 10 to 40% by weight of the soap mixture.

It should be explained that the Saponification Value is defined as the number of milligrams of potassium hydroxide required for the complete saponification of one gram of an oil or fat. The Saponification Value can be determined by the method described in "Chemical Technology and Analysis of Oils, Fats and Waxes" by Lewkowitsch and Warburton, published by Macmillan & Co., London, in 1921, at page 388.

Furthermore, the Iodine Value is defined as the percentage of iodine chloride absorbed by an oil or fat expressed in terms of iodine. The Iodine Value can be determined by the method described in the above treatise by Lewkowitsch and Warburton at page 401.

Furthermore, the Fatty Acid Titre Value is defined as the solidifying point in degrees centigrade of the mixed fatty acids obtained from a saponified oil or fat. The Titre Value can be determined by the method described in the above treatise by Lewkowitsch and Warburton at page 511.

Furthermore, the INS Factor is defined as the numerical difference between the Saponification Value and the Iodine Value, i.e. INS Factor equals Saponification Value minus Iodine Value.

The soap mixture can also contain saponified oils chosen from vegetable oils such as olive oil, arachis oil, cotton seed oil, maize oil, linseed oil, soyabean oil, castor oil, rice bran oil, mustard seed oil, sesame seed oil, jojuba oil, rosin (tall oil), sal oil, almond oil, hempseed oil, Japan tallow, kapok oil, nigerseed oil, olive kernel oil, perilla oil, poppyseed oil, rapeseed oil, safflower oil, shea nut butter, sunflower seed oil and ucuhuba butter oil, and animal oils such as bone grease, horse fat, Neat's foot oil, cod liver oil, herring oil, menhaden oil, porpoise oil, salmon oil, sardine oil and whale oil.

As an alternative, it is also possible to provide the mixture of fatty acid soaps which comprise the soap mixture by saponification of natural or synthetic free fatty acids. Individual saponified fatty acids of different chain lengths can be blended in appropriate amounts to provide the soap mixture or, alternatively, a mixture of free fatty acids, obtained for example by the splitting of fats or oils into their component glycerin and fatty acids, can be saponified together to provide the soap mixture.

The soap mixture can also contain soaps of natural or synthetic branched chain fatty acids.

It is also possible to employ any of the above-mentioned oils in a hardened or a dehydrated form wherever this is appropriate.

The amount of the soap mixture that can be incorporated into deodorant soap bars according to the invention is from 0.5 to 99.9% by weight. The preferred amount is within the range of from 5 to 95% by weight of the bar.

2. Unsaponified Fatty Acids

The soap bar can also optionally comprise $C_6$ to $C_{18}$ straight chain fatty acids in addition to the mixture of saponified fatty acids. The presence of these additional unsaponified fatty acids can improve the lathering properties of the soap bar, particularly when used in hard water areas. A preferred source of unsaponified fatty acid is that derived as a mixture from coconut oil.

The quantity of unsaponified fatty acids that can be present in the soap mix can form up to 15% by weight of the soap bar.

If more than 15% by weight of unsaponified fatty acids are employed in this manner, there may be a tendency for the soap bar to be too soft in use and to develop off-odours.

3. The Deodorant Composition

The characterisation of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

THE LIPOXIDASE TEST

In this test the capacity of a material to inhibit the oxidation of linoleic acid by lipoxidase (EC1.13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by by weight solution in ethanol of the material to be tested.

A solution of the enzyme lipxodase in the borate buffer and having an activity within the range of from 15,000 to 40,000 units per ml is prepared.

The activity of the lipxodiase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta$ OD) at 234 nm within the range of from 0.6 to 1.0 units per minute. The following ingredients are placed in two 3 ml cuvettes:

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100 (S_1 - S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

THE MORPHOLINE TEST

In this test the capacity of a material to depress the partial vapour pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g); and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No 2, 87–91 (1972) and by Jentzsch et al in "Z. Anal. Chem." 236, 96–118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1 - A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure $(p-p')/p$, is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g. coumarin (natural or synthetic), iso-eugenol, benzyl salicylate. The majority of components are in this category.

(2) Synthetic reaction products (products of reaction), mixtures of isomers and possibly homologues, e.g. α-iso-methyl ionone.

(3) Natural oils, gums and resins, and their extracts, e.g. patchouli oil, geranium oil, clove leaf oil, benzoin resinoid.

(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the soap bar of the invention to use components that, as well as satisfying the lipoxidase or morpholine tests, satisfy further conditions. These conditions are:

(i) there must be at least five components present, (ii) each of these components must be selected from at least four different chemical classes (to be defined below), (iii) a component from each of classes 1,2 and 4 must be present, (iv) at least 45%, preferably at least 50 and most preferably from 60 to 100%, by weight of the deodorant composition must comprise components, (v) a component is not considered to contribute to the efficacy of the deodorant composition if it is present in the deodorant composition at a concentration of less than 0.5% by weight, and (vi) a class is not considered to contribute to the efficacy of the deodorant composition if it is present in the deodorant composition at a concentration of less than 0.5% by weight.

Therefore, according to a preferred embodiment of the invention, there is provided a deodorant soap bar as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range 0.50 to 3.5.

Each component should be allocated to one of six classes. These classes are:

Class 1—Phenolic substances;
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume and Flavour Materials of Natural Origin" (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

| Class 1 - Phenolic Substances | | | |
|---|---|---|---|
| | LIC | RVR | m |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |

| Class 2 - Essential oils, extracts, resins, "synthetic" oils, (denoted by "AB") | | | |
|---|---|---|---|
| | LIC | RVR | m |
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |

| Class 3 - Aldehydes and Ketones | | | |
|---|---|---|---|
| | LIC | RVR | m |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl napthyl ketone | 100 | 0.96 | 170 |

| Class 4 - Polycyclic Compounds | | | |
|---|---|---|---|
| | LIC | RVR | m |
| Coumarin | 58 | 1.22 | 146 |
| 1,3,4,6,7,8-Hexahydro-4,6,6,7,8,8-hexamethyl cyclopenta-α-2-benzo-pyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |

| Class 5 - Esters | | | |
|---|---|---|---|
| | LIC | RVR | m |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |

| Class 6 - Alcohols | | | |
|---|---|---|---|
| | LIC | RVR | m |
| Dimyrcetol | 16 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant soap bar as herein defined wherein the amount of deodorant components in the deodorant composition present in the classes 1, 2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observer if the best results are to be obtained.

It should be explained that components present in the deodorant soap bar for purposes other than obtaining deodorant effects, for example an adjunct like the antioxidant included in a soap tablet for the stabilisation of the soap base, are excluded from the operation of the preceding instructions to the extent that the component is required for that other purpose. The levels at which adjuncts are conventionally present in soap bar compositions is well-established for established materials and readily determinable for new materials so that the application of the above exclusion presents no difficulty.

Deodorant compositions can be incorporated in soap bars according to the invention, at a concentration of from about 0.1 to about 10%, preferably from 0.5 to 5% and most preferably from 1 to 3% by weight.

It is apparent that if less than 0.1% of a deodorant composition is employed, then use of the soap bar is unlikely to provide a significant reduction in body malodour intensity. If more than 10% of a deodorant composition is employed, then use of the soap bar is unlikely to further reduce body malodour intensity beyond that observed at the 10% level.

4. Other Soap Adjuncts

Deodorant soap bars of the invention can contain other ingredients (adjuncts), for instance opacifiers such as titanium dioxide, lather boosters, lather controllers, inorganic salts such as sodium and magnesium sulphates and polyphosphates, chelating agents such as EDTA, moisturisers, plasticisers and thickeners, germicides and perfumes.

The deodorant toilet soap bar also comprises from 5 to 20%, preferably 7 to 15% by weight of water. This water may be present in the saponified soaps which constitute part of the soap mixture, or it can be incorporated into the soap bar as a separate ingredient.

The total amount of soap adjuncts that can be incorporated into the deodorant soap bar according to the invention will normally form the balance of the bar formulation after accounting for the main components as herein defined. The other soap adjuncts will accordingly form from 0 to 99.4%, preferably from 5 to 95% by weight of the composition.

The invention is further illustrated by the following four examples of soap bar formulations of which mixture A is a 55/45/7.5 soap base, mixture B is a 80/20/5 soap base, mixture C is a 80/20 soap and mixture D is a 70/30 soap base. These can be used as a basis for incorporation of a deodorant composition at a concentration of from 0.1 to 10% by weight to form deodorant soap bars according to the invention.

| SOAP MIXTURE | FORMULATION | | | |
|---|---|---|---|---|
| | A | B | C | D |
| | PERCENT BY WEIGHT | | | |
| sodium caprylate | 2.90 | — | — | 0.68 |
| sodium caprate | 2.49 | 1.19 | 1.19 | 1.78 |
| sodium laurate | 17.42 | 8.04 | 8.04 | 11.93 |
| sodium myristate | 8.46 | 5.93 | 5.93 | 5.16 |
| sodium palmitate | 17.42 | 22.26 | 22.26 | 27.41 |
| sodium stearate | 9.54 | 13.37 | 13.37 | 2.37 |
| sodium oleate | 21.57 | 29.63 | 29.63 | 28.85 |
| sodium linoleate | 2.74 | 2.79 | 2.79 | 6.43 |

| NON-SOAP INGREDIENTS (ADJUNCTS) | | | | |
|---|---|---|---|---|
| free fatty acid | 6.1 | 4.1 | — | — |
| butylated hydroxy toluene | 0.013 | 0.08 | — | — |
| Na$_2$HPO$_4$ | 0.17 | 0.17 | — | — |
| sodium EDTA | 0.024 | 0.024 | 0.05 | 0.05 |
| EHDP | 0.018 | 0.018 | 0.036 | 0.036 |

| NON-SOAP INGREDIENTS (ADJUNCTS) -continued | | | | |
|---|---|---|---|---|
| titanium dioxide | 0.24 | 0.31 | 0.25 | 0.25 |
| water and salts | 10.895 | 12.088 | 16.454 | 15.054 |

PROCESS FOR PREPARING DEODORANT SOAP COMPOSITIONS

The process for preparing deodorant soap bars thereby employing a deodorant composition as a means for inhibiting body malodour development comprises mixing with fatty acid soaps and soap adjuncts, as appropriate, from 0.1 to 10% by weight of a deodorant composition to provide a deodorant soap bar which is capable of reducing odour intensity by at least 0.50 (i.e. a deodorant value within the range of from 0.50 and 3.5) as measured by the Deodorant Value Test. The selection of the fatty acid soaps for the soap mixture, the soap adjuncts and their respective amounts employed in the process of the invention will depend upon the required properties of the soap bar.

Usually, it is convenient to add the deodorant composition to the soap mixture and other ingredients at a stage towards the end of its manufacture so that loss of any volatile ingredients such as may occur during a heating step is minimised. Usually, the deodorant composition is incorporated before extruding and stamping the soap to form toilet soap bars.

It is furthermore usual to incorporate the deodorant composition in such a manner that it is thoroughly mixed with the other ingredients and is uniformly distributed throughout the soap bar, although, as an alternative, it is possible to incorporate the deodorant composition in a soap bar having a striped or marbled construction.

The deodorant toilet soap bar of the invention is to be employed particularly for suppressing human body malodour by applying it in a washing mode to the skin. It is particularly effective when applied in this way to the regions of the skin where apocrine sweat glands are most abundant, notably in the groin, axilla, anal and genital regions and in the areola of the nipple.

SPECIFIC EXAMPLES OF THE INVENTION

The invention is illustrated by the following examples, in which all parts and percentages are by weight.

In each of Examples 1 to 6 a deodorant composition was prepared by mixing the components and other ingredients listed in the relevant Deodorant Composition, which gives the amount of components in each class. Test soap bars (containing 1.5% of the deodorant composition) representing deodorant soap bars of the invention and control soap bars were prepared using soap bar Formulation B (a 80/20/5 superfatted bar as hereinbefore defined) and tested as described in the Deodorant Value Test given above, with the results as shown in each instance.

EXAMPLE 1

The formulation of the Deodorant Composition 1 is as follows:

| Deodorant Composition 1 | | | |
|---|---|---|---|
| | Parts | Class | Total in class |
| Components | | | |

-continued

| Deodorant Composition 1 | Parts | Class | Total in class |
|---|---|---|---|
| iso-Amyl salicylate | 5.0 | 1 | |
| Benzyl salicylate | 4.0 | 1 | 10.25 |
| LRG 201 | 1.25 | 1 | |
| Bergamot AB 430 | 15.0 | 2 | |
| Geranium AB 76 | 4.0 | 2 | 20.7 |
| Opoponax resinoid | 1.7 | 2 | |
| 1,3,4,6,7,8-Hexahydro-4,6,6,7,-8,8-hexamethylcyclopenta-γ-2-benzopyran | 10.0 | 4 | 10.0 |
| o-t-Butylcyclohexyl acetate | 0.5 | 5 | |
| | | | 4.25 |
| Diethyl phthalate | 3.75 | 5 | |
| Nonanolide-1,4 | 0.2* | (5) | |
| Ingredients | | | |
| Amber AB 358 | 3.0 | | |
| Benzyl alcohol | 0.15 | | |
| Cedar atlas oil | 5.0 | | |
| Citronellol | 7.0 | | |
| Citronella oil | 16.1 | | |
| Citronellyloxyacetaldehyde | 0.5 | | |
| Hexyl aldone | 0.7 | | |
| Jasmin AB 284 | 12.0 | | |
| Orange oil sweet | 8.0 | | |
| 10-Undecen-1-al | 0.15 | | |
| Vetyvert oil | 2.0 | | |
| | 100.0 | | |

*eliminated from calculation - below threshold value of 0.5%

| | |
|---|---|
| Total amount of components | 45.2 |
| Number of components present | 9 |
| Average amount of each component | 5.0 |
| Number of classes represented | 4 |

| Results of Deodorant Value Test 1 | Control Bar | Test Bar |
|---|---|---|
| Average scores | 3.46 | 2.93 |
| Deodorant value | | 0.53 |

EXAMPLE 2

The formulation of Deodorant Composition 2 is as follows:

| Deodorant Composition 2 | Parts | Class | Total in class |
|---|---|---|---|
| Components | | | |
| Carvacrol | 3.5 | 1 | |
| | | | 4.5 |
| Thyme oil red | 1.0 | 1 | |
| Bergamot AB 37 | 20.0 | 2 | |
| Pomeransol AB 413 | 6.0 | 2 | 30.0 |
| Petitgrain oil | 4.0 | 2 | |
| 6-Acetyl-1,1,3,4,4,6-hexa-methyl-tetrahydro-naphthalene | 3.0 | 3 | 8.0 |
| β-Methyl naphthyl ketone | 5.0 | 3 | |
| 3a-Methyl-dodecahydro-6,6,9a-trimethyl naphtho-2(2,1-b) furan | 0.25* | (4) | |
| β-Naphthol methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |
| Lime AB 402 | 10.0 | | |
| Lavendin oil | 4.0 | | |
| l-Menthol | 8.0 | | |

| Deodorant Composition 2 | Parts | Class | Total in class |
|---|---|---|---|
| Neroli AB 78 | 6.0 | | |
| Orange oil sweet | 5.0 | | |
| | 100.0 | | |

*eliminated from calculation - below threshold value of 0.5%

| | |
|---|---|
| Total amount of components | 51.5 |
| Number of components present | 8 |
| Average amount of each component | 6.4 |
| Number of classes represented | 4 |

| Results of Deodorant Value Test 2 | Control bar | Test bar |
|---|---|---|
| Average scores | 3.34 | 2.73 |
| Deodorant Value | | 0.61 |

EXAMPLE 3

The formulation of Deodorant Composition 3 is as follows:

| Deodorant Composition 3 | Parts | Class | Total in class |
|---|---|---|---|
| Components | | | |
| Mousse de chene Yugo | 1.25 | 1 | |
| | | | 11.25 |
| Pimento leaf oil | 10.0 | 1 | |
| Benzoin Siam resinoids | 5.0 | 2 | |
| Bergamot AB 430 | 15.0 | 2 | 25.0 |
| Geranium oil | 5.0 | 2 | |
| p-t-Amylcyclohexanone | 5.0 | 3 | |
| | | | 17.0 |
| α-iso-Methyl ionone | 12.0 | 3 | |
| Coumarin | 4.0 | 4 | |
| 1,3,4,6,7,8-Hexahydro-4,6,6,7,8,8-hexamethyl-cyclopenta-γ-2-benzopyran | 3.0 | 4 | 7.0 |
| Diethyl phthalate | 4.35 | 5 | 4.35 |
| Ingredients | | | |
| Hercolyn D | 12.25 | | |
| Lavendin oil | 10.0 | | |
| Musk ambrette | 3.0 | | |
| Rosenta AB 380 | 10.0 | | |
| Rose-D-oxide | 0.15 | | |
| | 100.0 | | |

| | |
|---|---|
| Total amount of components | 64.6 |
| Number of components present | 10 |
| Average amount of each component | 6.5 |
| Number of classes represented | 5 |

| Results of Deodorant Value Test 3 | Control bar | Test bar |
|---|---|---|
| Average scores | 3.04 | 2.47 |
| Deodorant Value | | 0.57 |

EXAMPLE 4

The formulation of Deodorant Composition 4 is as follows:

| Deodorant Composition 4 | | | |
|---|---|---|---|
| Components | Parts | Class | Total in class |
| Ethyl vanillin | 0.2* | (1) | |
| iso-Eugenol | 5.0 | 1 | |
| LRG 201 | 1.25 | 1 | 6.25 |
| Bergamot AB 430 | 8.0 | 2 | |
| Patchouli oil | 7.0 | 2 | 15.0 |
| 2-n-Heptylcyclopentanone | 0.5 | 3 | |
| α-iso-Methyl ionone | 5.0 | 3 | 5.5 |
| β-Naphthol methylether | 7.5 | 4 | 7.5 |
| p-t-Butylcyclohexyl acetate | 4.3 | 5 | |
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |
| Citronella oil | 6.0 | | |
| Green Herbal AB 502 | 15.0 | | |
| Indole | 1.5 | | |
| Rosenta AB 380 | 6.0 | | |
| Sandalone | 4.0 | | |
| γ-Undecalactone | 0.5 | | |
| | 100.0 | | |

*eliminated from calculation - below threshold value of 0.5%

| Total amount of components | 66.8 |
|---|---|
| Number of components present | 14 |
| Average amount of each component | 4.8 |
| Number of classes represented | 6 |

| Results of Deodorant Value Test 4 | | |
|---|---|---|
| | Control bar | Test bar |
| Average scores | 3.25 | 2.10 |
| Deodorant Value | | 1.15 |

EXAMPLE 5

The formulation of Deodorant Composition 5 is as follows:

| Deodorant Composition 5 | | | |
|---|---|---|---|
| Components | Parts | Class | Total in class |
| Benzyl salicylate | 15.0 | 1 | |
| Mousse de chene Yugo | 6.0 | 1 | 21.0 |
| Bergamot AB 430 | 15.0 | 2 | 15.0 |
| 6-Acetyl-1,3,3,4,4,6-hexamethyl tetrahydronaphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b) furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |

| Deodorant Composition 5 -continued | | | |
|---|---|---|---|
| | Parts | Class | Total in class |
| Trichloromethyl phenyl carbinyl acetate | 0.2 | | |
| | 100.0 | | |

*eliminated from calculation - below threshold value for a component of 0.5%

| Total amount of components | 63.29 |
|---|---|
| Number of components present | 7 |
| Average amount of each component | 9.0 |
| Number of classes represented | 6 |

| Results of Deodorant Value Test 5 | | |
|---|---|---|
| | Control bar | Test bar |
| Average scores | 3.30 | 2.70 |
| Deodorant Value | | 0.60 |

EXAMPLE 6

The formulation of Deodorant Composition 6 is as follows:

| Deodorant Composition 6 | | | |
|---|---|---|---|
| Components | Parts | Class | Total in class |
| Clove leaf oil | 10.0 | 1 | |
| LRG 201 | 1.25 | 1 | 11.25 |
| Petitgrain oil | 10.0 | 2 | 10.0 |
| p-t-Butyl-α-methyl hydro cinnamic aldehyde | 15.0 | 3 | 15.0 |
| 3a-Methyl-dodecahydro-6,6,9a-trimethylnaphtho-2(2,1-b) furan | 0.5 | 4 | 0.5 |
| o-t-Butylcyclohexyl acetate | 2.0 | 5 | |
| Diethyl phthalate | 9.25 | 5 | 21.25 |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |

| Total amount of components | 68.0 |
|---|---|
| Number of components present | 9 |
| Average amount of each component | 7.6 |
| Number of classes represented | 6 |

| Results of Deodorant Value Test 6 | | |
|---|---|---|
| | Control bar | Test bar |
| Average scores | 3.25 | 2.33 |
| Deodorant Value | | 0.92 |

EXAMPLE 7a

Example 2 employing Deodorant Composition 2 was repeated except that the soap bars were prepared using soap bar Formulation C (a 80/20 non-superfatted bar as hereinbefore described).

| Results of Deodorant Value Test 7a | | |
|---|---|---|
| | Control bar | Test bar |
| Average scores | 3.30 | 2.60 |
| Deodorant value | | 0.70 |

EXAMPLE 7b

Example 2 employing Deodorant Composition 2 was also repeated using a non-superfatted soap bar in which the soap was entirely tallow soap.

| Results of Deodorant Value Test 7b | | |
|---|---|---|
| | Control bar | Test bar |
| Average scores | 3.30 | 2.72 |
| Deodorant value | | 0.58 |

EXAMPLE 8

Example 4 employing Deodorant Composition 4 was repeated except that the soap bars were prepared using soap bar Formulation A (a 55/45/7.5 superfatted bar as hereinbefore described).

| Results of Deodorant Value Test 8 | | |
|---|---|---|
| | Control bar | Test bar |
| Average scores | 3.30 | 1.64 |
| Deodorant value | | 1.66 |

APPENDIX

The following glossary provides further information, including the suppliers' names, which will aid identification of some of the aforementioned deodorant components and ingredients.

| | |
|---|---|
| Dimyrcetol | Dimyrcetol (IFF) |
| Hercolyn D | Tetrahydro abietate + dihydro abietate (HP) |
| LRG 201 | Oakmoss speciality (RB) |
| Pelargene | Pelargene (PPL) |
| Rose-D-Oxide | Rose oxide synthetic (PPL) |
| Sandalone | Sandalone (PPL) |
| Perfume Houses | |
| HP | Hercules Powder Co. |
| IFF | International Flavour & Fragrances Inc. |
| RB | Roure Bertrand |
| PPL | Proprietary Perfumes Limited |

All materials which are classified by a name and number, such as those having the 'AB' notation, are obtainable from Proprietary Perfumes Limited.

What is claimed is:

1. A deodorant toilet soap bar comprising:
 (i) from 0.5 to 99.9% by weight of a soap mixture;
 (ii) from 0 to 15% by weight of $C_6$ to $C_{18}$ straight chain fatty acids; and
 (iii) from 0.1 to 10% by weight of a deodorant composition comprising from 45 to 100% by weight of deodorant active components, said components having a lipoxidase-inhibiting capacity of at least 50% or a Raoult variance ratio of at least 1.1, said components being classified into six classes consisting of:
 Class 1: phenolic substances
 Class 2: essential oils, extracts, resins and synthetic oils
 Class 3: aldehydes and ketones
 Class 4: polycyclic compounds
 Class 5: esters
 Class 6: alcohols
provided that where a component can be classified into more than one class, it is placed in the lower or lowest numbered class;
 said components being so selected that
 (a) the deodorant composition contains at least five components of which at least one must be selected from each of Class 1, Class 2 and Class 4;
 (b) the deodorant composition contains components from at least 4 of the 6 classes, and
 (c) any component present in the deodorant composition at a concentration of less than 0.5% by weight of said composition is eliminated from the requirements of (a) and (b), said deodorant composition having a deodorant value of from 0.50 to 3.5 as measured by the Deodorant Value Test.

2. The deodorant soap bar of claim 1, wherein the deodorant composition has a deodorant value of from 0.90 to 3.5 as measured by the Deodorant Value Test.

3. The deodorant soap bar of claim 1, wherein the deodorant composition has a deodorant value of from 1.10 to 3.5 as measured by the Deodorant Value Test.

4. The deodorant soap bar of claim 1, wherein the soap mixture comprises a soap of lauric acid, a soap of myristic acid, a soap of palmitic acid, a soap of stearic acid and a soap of oleic acid.

5. The deodorant soap bar of claim 1, wherein the soap mixture comprises from about 2 to about 38% by weight of a soap of lauric acid, from about 0.5 to about 25% by weight of a soap of myristic acid, from about 5 to about 45% by weight of a soap of palmitic acid, from about 1 to about 25% by weight of a soap of stearic acid and from about 10 to about 40% by weight of a soap of oleic acid.

6. The deodorant soap bar of claim 1, wherein the soap mixture comprises at least two saponified naturally occurring oils, the first oil having a saponification value of from 170 to 220, an iodine value of from 25 to 70, a fatty acid titre value of from 30° to 55° C. and an INS value of from 120 to 210, the first saponified oil comprising from about 15 to about 50 parts by weight of a soap of palmitic acid and from about 2 to about 20 parts by weight of a soap of stearic acid; and a second oil having a saponification value of from 240 to 265, an iodine value of from 5 to 20, a fatty acid titre value of from 15° to 30° C. and an INS value of from 220 to 225, the second saponified oil comprising from about 40 to 50 parts by weight of a soap of lauric acid and from about 10 to about 25 parts by weight of a soap of myristic acid.

7. The deodorant soap bar of claim 1, wherein the amount of deodorant components present in said class comprising phenolic substances and said class comprising essential oils, extracts, resins and synthetic oils and said class comprising polycyclic compounds, is at least 1% by weight of the deodorant composition for each of said classes, and the amount of perfume components present in said further class chosen from the remaining three classes is at least 1% by weight of the deodorant composition.

8. The deodorant soap bar of claim 1, wherein the average concentration of all such components present is at least 5% by weight where four of said classes is represented, or at least 4.5% by weight where five or six of said classes is represented.

9. The deodorant soap bar of claim 1, wherein the amount of deodorant components present in said class comprising phenolic substances and said class comprising essential oils, extracts, resins and synthetic oils and said class comprising polycyclic compounds, is at least 3% by weight of the deodorant composition for each of said classes and the amount of deodorant components present in said further class chosen from the remaining three classes is at least 3% by weight of the deodorant composition.

10. The deodorant soap bar of claim 3, wherein at least five of the classes is represented.

11. The deodorant soap bar of claim 3, wherein all six classes are represented.

12. The deodorant perfume of claim 6, wherein the said deodorant components are chosen from:

Class 1—Phenolic substances
  iso-Amyl salicylate
  Benzyl salicylate
  Carvacrol
  Clove leaf oil
  Ethyl vanillin
  iso-Eugenol
  LRG 201
  Mousse de chene Yugo
  Pimento leaf oil
  Thyme oil red
Class 2—Essential oils, extracts, resins, "synthetic" oils, (denoted by "AB")
  Benzoin Siam resinoids
  Bergamot AB 37
  Bergamot AB 430
  Geranium AB 76
  Geranium oil
  Opoponax resinoid
  Patchouli oil
  Petitgrain oil
  Pomeransol AB 314
Class 3—Polycyclic compounds
  Coumarin
  1,3,4,6,7,8-Hexahydro-4,6,6,7,8,9-hexamethyl cyclopenta-γ-2-benzopyran
  3a-Methyl-dodecahydro-6,6,9a-trimethylnaphtho-(2,1-b)furan
  β-Naphthyl methyl ether
Class 4—Aldehydes and ketones
  6-Acetyl-1,1,3,4,4,6-hexamethyltetrahydronaphthalene
  p-t-Amyl cyclohexanone
  p-t-Butyl-α-methyl hydrocinnamic aldehyde
  2-n-Heptylcyclopentanone
  α-iso-Methyl ionone
  α-Methyl naphthyl ketone
Class 5—Esters
  o-t-Butylcyclohexyl acetate
  p-t-Butylcyclohexyl acetate
  Diethyl phthalate
  Nonanediol-1,3-diacetate
  Nonanolide-1:4
  i-Nonyl acetate
  i-Nonyl formate
Class 6—Alcohols
  Dimyrcetol
  Phenylethyl alcohol
  Tetrahydromuguol.

13. A process for preparing the deodorant soap bar of claim 1, which comprises blending a soap mixture with said deodorant composition and thereafter extruding and stamping the soap to provide the deodorant soap bar.

14. A method for suppressing human body malodour which comprises applying to the skin in the region of apocrine sweat glands a malodour reducing amount of a deodorant composition comprising from 45 to 100% by weight of deodorant active components, said components having a lipoxidase-inhibiting capacity of at least 50% or a Raoult variance ratio of at least 1.1, said components being classified into six classes consisting of:
  Class 1: phenolic substances
  Class 2: essential oils, extracts, resins and synthetic oils
  Class 3: aldehydes and ketones Class 4: polycyclic compounds
  Class 5: esters
  Class 6: alcohols,
provided that where a component can be classified into more than one class, it is placed in the lower or lowest numbered class;
said components being so selected that
  (a) the deodorant composition contains at least five components of which at least one must be selected from each of Class 1, Class 2 and Class 4;
  (b) the deodorant composition contains components from at least 4 of the 6 classes, and
  (c) any component present in the deodorant composition at a concentration of less than 0.5% by weight of said composition is eliminated from the requirements of (a) and (b).

15. The method according to claim 14, wherein the deodorant composition further includes a cosmetically and physiologically acceptable compatible carrier; the weight ratio of deodorant composition to carrier being from 1:90 to 1 to 999.

16. The method according to claim 14, wherein the carrier is a soap mixture.

* * * * *